(12) United States Patent
Fisher et al.

(10) Patent No.: US 9,149,620 B2
(45) Date of Patent: Oct. 6, 2015

(54) VENOUS ACCESS PORT ASSEMBLY AND METHOD OF ASSEMBLY

(75) Inventors: Mark S. Fisher, Sellersville, PA (US); W. Shaun Wall, North Wales, PA (US)

(73) Assignee: MEDICAL COMPONENTS, INC., Harleysville, PA (US)

( * ) Notice: Subject to any disclaimer, the term of this patent is extended or adjusted under 35 U.S.C. 154(b) by 880 days.

(21) Appl. No.: 12/607,202

(22) Filed: Oct. 28, 2009

(65) Prior Publication Data
US 2010/0106094 A1   Apr. 29, 2010

Related U.S. Application Data

(60) Provisional application No. 61/108,935, filed on Oct. 28, 2008.

(51) Int. Cl.
*A61M 39/02* (2006.01)
*A61M 39/00* (2006.01)

(52) U.S. Cl.
CPC .... *A61M 39/0208* (2013.01); *A61M 2039/0036* (2013.01); *A61M 2039/0063* (2013.01); *A61M 2039/0072* (2013.01); *A61M 2039/0211* (2013.01); *A61M 2039/0229* (2013.01)

(58) Field of Classification Search
CPC ................ A61M 39/0208; A61M 2039/0229; A61M 2039/0214; A61M 2039/0217; A61M 2039/0211; A61M 2039/0072; A61M 2039/0063; A61M 2039/0036
USPC ................ 604/288.01–288.04, 890.1, 891.1
See application file for complete search history.

(56) References Cited

U.S. PATENT DOCUMENTS

| | | | |
|---|---|---|---|
| 3,858,162 A | * | 12/1974 | Mai et al. ...................... 439/612 |
| 4,704,103 A | | 11/1987 | Stober et al. |
| 4,762,517 A | | 8/1988 | McIntyre et al. |
| 4,778,452 A | | 10/1988 | Moden et al. |

(Continued)

FOREIGN PATENT DOCUMENTS

| | | |
|---|---|---|
| FR | 2586569 A1 | 3/1987 |
| WO | WO9701370 A1 | 1/1997 |

(Continued)

OTHER PUBLICATIONS

International Preliminary Report on Patentability; International Application No. PCT/SU2009/062283; International Filing Date: Oct. 28, 2009; 6 pages.

*Primary Examiner* — Bhisma Mehta
*Assistant Examiner* — Larry R Wilson
(74) *Attorney, Agent, or Firm* — Buchanan Ingersoll & Rooney PC

(57) ABSTRACT

An implantable port assembly (10) having a lower housing (12) and an upper housing (14) and at least one chamber (20,22) and a corresponding septum (16,18) associated therewith. The upper housing (14) includes a plurality of latch arms (30) depending therefrom that latch with corresponding catches (34) of the lower housing for mechanically securing the assembly together during bonding or welding. Each septum (16,18) includes a peripheral flange (40) held in compression by and between the upper and lower housings (14, 12) upon and after assembly. In a dual port assembly (10), a pair of septa (16,18) are disposed side-by-side with overlapping flanges (54), and the upper housing (14) includes posts (52) extending through apertures (54) through the overlapping flanges (56) that extend into holes (58) in the lower housing (12).

20 Claims, 3 Drawing Sheets

(56) References Cited

U.S. PATENT DOCUMENTS

| | | |
|---|---|---|
| 4,802,885 A | 2/1989 | Weeks et al. |
| 5,045,060 A | 9/1991 | Melsky et al. |
| 5,137,529 A | 8/1992 | Watson et al. |
| 5,185,003 A | 2/1993 | Brethauer |
| 5,213,574 A | 5/1993 | Tucker |
| 5,360,407 A | 11/1994 | Leonard |
| 5,399,168 A | 3/1995 | Wadsworth, Jr. et al. |
| 5,718,682 A | 2/1998 | Tucker |
| 5,833,654 A | 11/1998 | Powers et al. |
| 5,989,216 A | 11/1999 | Johnson et al. |
| 6,086,555 A | 7/2000 | Eliasen et al. |
| 6,113,572 A | 9/2000 | Gailey et al. |
| 6,190,352 B1 | 2/2001 | Haarala et al. |
| 6,213,973 B1 | 4/2001 | Eliasen et al. |
| 6,527,754 B1 | 3/2003 | Tallarida et al. |
| 7,186,236 B2 | 3/2007 | Gibson et al. |
| 2004/0204692 A1 | 10/2004 | Eliasen |
| 2005/0171502 A1 | 8/2005 | Daly et al. |
| 2005/0222582 A1* | 10/2005 | Wenchell ............... 606/108 |
| 2007/0219510 A1 | 9/2007 | Zinn et al. |
| 2007/0270770 A1* | 11/2007 | Bizup ............... 604/288.02 |
| 2009/0118683 A1* | 5/2009 | Hanson et al. ......... 604/288.01 |

FOREIGN PATENT DOCUMENTS

| | | |
|---|---|---|
| WO | WO98/31417 A2 | 7/1998 |
| WO | WO2006/116438 A2 | 11/2006 |

* cited by examiner

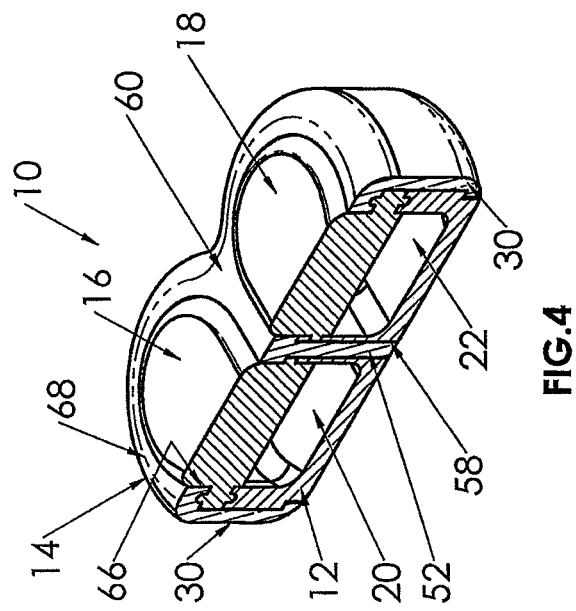
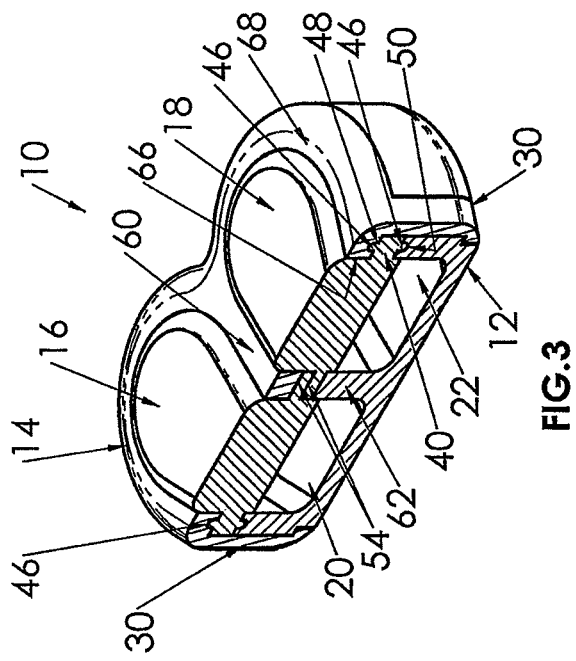

VENOUS ACCESS PORT ASSEMBLY AND METHOD OF ASSEMBLY

CROSS-REFERENCE TO RELATED APPLICATIONS

This application claims the benefit of U.S. Provisional Patent Application Ser. No. 61/108,935 filed Oct. 28, 2008.

FIELD OF THE INVENTION

This relates to the field of medical devices and more particularly to implantable venous access port assemblies.

BACKGROUND OF THE INVENTION

Infusion ports for the infusion and/or withdrawal of fluids from a patient are well-known, secured to the proximal end of an implanted catheter. These ports are typically used for drug infusion or small amounts of blood withdrawal, where large flows of fluid are not required. Implantable venous access ports have the advantage that they can remain within the patient for prolonged periods of time, permitting multiple use and decreasing the risk for associated infection. The ports are assemblies of a needle-impenetrable housing with a discharge port in fluid communication with the catheter and the reservoir or chamber within the port housing, and provide a subcutaneous self-sealing septum that defines an access site for multiple needle sticks through the covering skin tissue of the patient, through the septum and into the reservoir, without the need to continuously search for new access sites. The septum is comprised of material such as silicone elastomer that self-seals each time as a needle is withdrawn. Examples of such ports are disclosed, for example, in U.S. Pat. Nos. 4,704,103; 4,762,517; 4,778,452; 5,185,003; 5,213,574 and 5,637,102; and 6,113,572. Another catheter infusion port is disclosed in U.S. Patent Publication No. US 2006/0184142 published on Aug. 17, 2006 (Ser. No. 11/335,369 filed Jan. 19, 2006).

Some ports are in use, known as dual ports or multi-ports. These provide two or more septa and internal chambers, all corresponding to different lumens of the attached catheter via respective separate discharge ports or alternatively, separate passageways in a single stem for communication with separate lumens of a dual or multi-lumen catheter, such as in U.S. Pat. No. 5,360,407.

Typically, a port housing includes a base and a cap that together cooperate to secure the needle-penetrable septum within the assembly by compressing a seating flange of the septum in a seat of the housing base. The housings of many such ports are bonded (or welded) together, with fixtures holding the cap to the base as the bonding agent dries (or as welding is performed), to compress the septum flange to assure compression of the septum flange after manufacturing is completed. One manner of securing a cap to a base is disclosed in U.S. Patent Publication No. US 2007/0270770 published on Nov. 22, 2007 wherein the housing cap and base mechanically self-retain to compress the septum flange as the bonding agent cures. In this port, horizontal rib segments are formed on either the interior surface of the cap or the exterior surface of the base, while the other thereof provides grooves for the rib segments, such that the cap is snap-fitted to the base by this fastening arrangement to compress the septum flange between the cap and base, thus eliminating the necessity of using fixture tooling during manufacturing while the bonding agent dries.

It is desired to provide a venous access port assembly that is assuredly secured together in an assuredly sealed manner.

BRIEF SUMMARY OF THE INVENTION

Briefly, the present invention is an implantable venous access port assembly having a housing defining at least one chamber or reservoir, at least one septum associated with the chamber, and a discharge end having at least one passageway therethrough in fluid communication with a respective at least one chamber for fluid flow into a corresponding lumen of a catheter affixable to a discharge stem affixed to the port housing assembly. The housing is an assembly that includes a base or lower housing and a cap or upper housing securable thereto about the at least one septum. The upper housing includes at least two latching sections such as latch arms depending from sides thereof, to latchingly engage corresponding latching sections or catches defined on or by the lower housing upon assembly thereto, in a manner compressing a flange of the at least one septum. A method of assembly of the present invention comprises the steps of mechanically fastening the upper and lower housings to each other by latch arms, in a manner compressing therebetween a peripheral flange of each septum.

In a preferred embodiment of a dual port assembly of the present invention, the septa include peripheral flanges that are compressed between the upper and lower housings upon assembly, which flanges further include ridges projecting from upper and lower surfaces of the peripheral flanges that are disposed in corresponding grooves in the upper and lower housings, all to secure the septa in a sealed relationship about the upper openings to the chambers. Between the two septa are overlapping flanges of each; preferably, the upper housing includes an array of depending posts extending through openings in the overlapping flanges and into corresponding holes in the lower housing upon assembly. The latch arms, the flange-compressing structure and the post array all serve to secure the housings to each other in a manner compressing the peripheral flanges of the septa while bonding agent cures or during ultrasonic welding, eliminating the necessity of fixtures in the assembly process, and also serve to secure the septa in a sealed relationship with the housings during needle penetration and withdrawal.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIGS. 3 and 4 are cross-sectional views taken along planes 3-3 and 4-4 of FIG. 1.

DETAILED DESCRIPTION OF THE INVENTION

Figure 1:
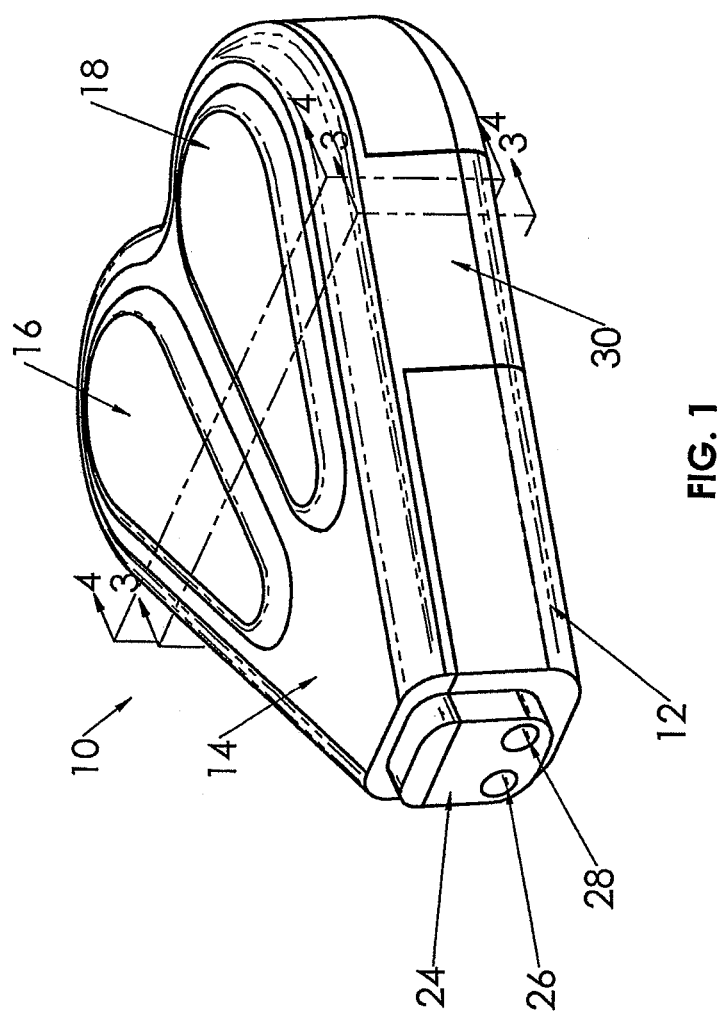
FIG. 1 is an isometric view of the port assembly of the present invention.

Certain terminology is used herein for convenience only and is not to be taken as a limitation on the present invention. The terminology includes the words specifically mentioned, derivatives thereof and words of similar import. The embodiment illustrated below is not intended to be exhaustive or to limit the invention to the precise form disclosed. This embodiment is chosen and described to best explain the principle of the invention and its application and practical use and to enable others skilled in the art to best utilize the invention.

Venous access port assembly 10 of the Figures includes a lower or base housing 12, an upper or cap housing 14 and two septa 16,18 associated with respective chambers or reservoirs 20,22 disposed side-by-side in the assembly 10. A discharge end 24 is seen having a pair of passageways 26,28 to which a pair of discharge stem conduits (not shown) will be associated upon assembly of a discharge stem to the discharge end, to establish fluid communication between chambers 20,22 and respective lumens of a dual lumen catheter (not shown) affixable to the discharge stem at discharge end 24. Each septum 16,18 is made of self-sealing material so as to be needle-penetrable and yet close off and seal after a respective needle (not shown) is withdrawn; such a material may be silicone elastomer. The lower and upper housings 12,14 are made of needle-impenetrable material, such as polysulfone or polypropylene.

Upper housing 14 is affixable to lower housing 12 by at least two latching sections, preferably latch arms 30, one on each side of the upper housing, each of which has a latch section 32 at a free end thereof which establishes a latching connection with a corresponding latching section or catch 34 of the lower housing upon assembly; four such latch arms 30 are shown in this embodiment. Prior to latching, septa 16,18 are seated in septum seats 36,38 of lower housing 12 such that peripheral flanges 40 of the septa are compressed between compression surfaces 42 of upper housing 14 and compression surfaces 44 of lower housing 12 to establish a peripheral seal about each chamber 20,22 in a manner resistant to stresses caused by penetration of needles through the respective septa and withdrawal therefrom. Bonding or ultrasonic welding is preferably utilized to establish a hermetic seal in addition to the latching arrangement just described; the latching arrangement serves to eliminate the necessity of fixtures housing the housings together while the bonding agent cures or during ultrasonic welding.

Figure 2:
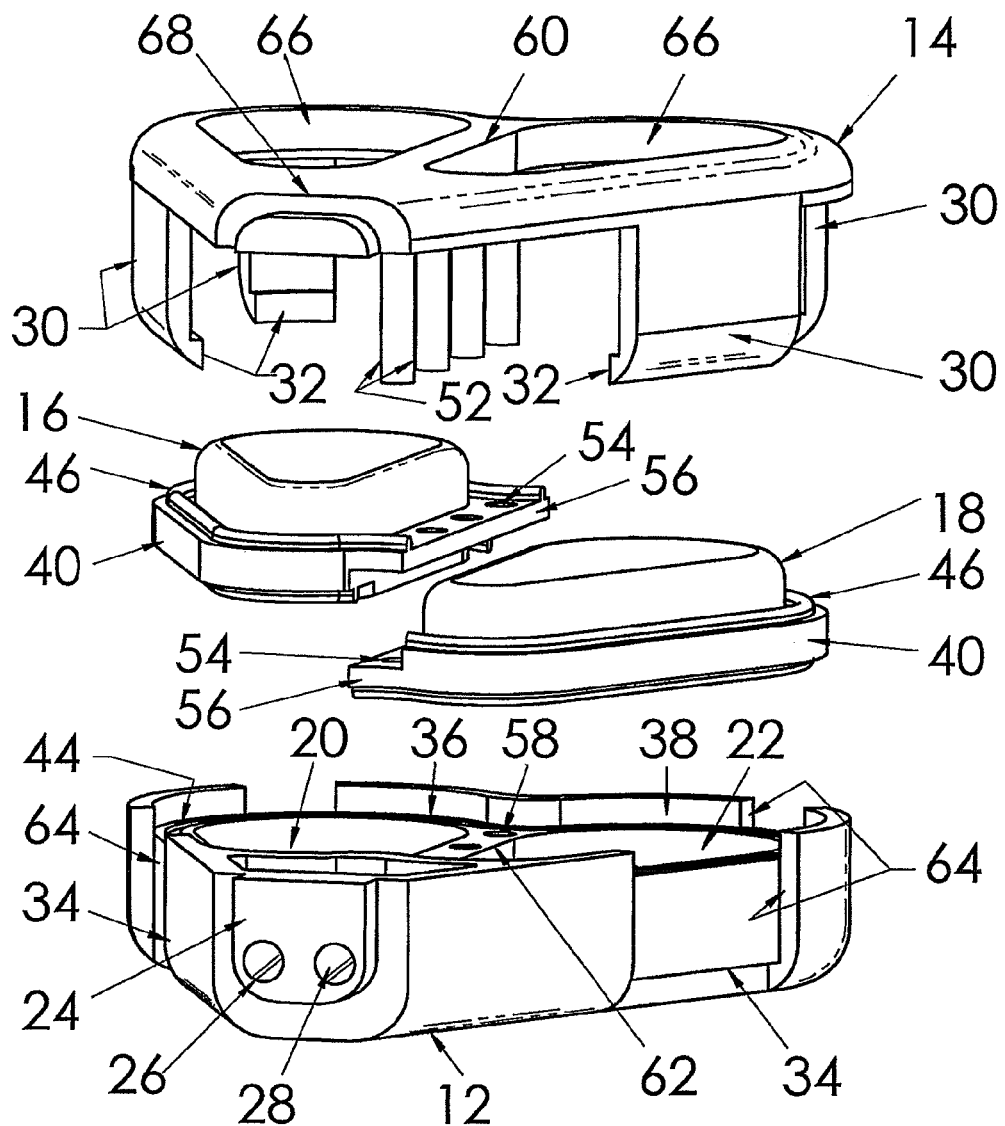
FIG. 2 is an exploded view of the port assembly of FIG. 1.

It can be seen that peripheral ridges 46 are provided on upper and lower surfaces of the peripheral flanges 40 of the respective septa that seat in corresponding grooves 48 of upper housing 14 and grooves 50 of lower housing 12, facilitating securement of the septa in position. Preferably, septa 16,18 include straight side portions adjacent each other and have overlapping flanges 56 therealong. It can also be seen that an array of posts 52 (FIGS. 2 and 4) depend from a medial rib 60 of upper housing 14 through apertures 54 in the overlapping flanges 56 and into corresponding holes 58 in a medial rib 62 of lower housing 12, to further secure the septa in place during bonding or welding, and later during needle penetration and withdrawal. Preferably, latch arms 30 are disposed along respective recesses 64 of lower housing 12 thus providing a smooth continuous exterior surface to the port assembly. Further, preferably, top portions of septa 16,18 protrude upwardly through openings 66 in upper housing 14 and beyond the top surface 68 thereof, so that the location of the septa may be discerned by tactile feel or palpation by the practitioner to identify the target site for needle penetration.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A venous access port, comprising:
    a housing,
    at least two self-sealing septa for infusion by needle, the two self-sealing septa each having a peripheral flange and a raised and rounded central portion relative thereto, the raised and rounded central portion defining a subcutaneous, self-sealing access site for multiple needle sticks,
    at least one chamber associated with each respective septum, and
    a discharge end for a discharge stem affixed thereat for connection with a catheter proximal end, the discharge end having at least one passageway therethrough associated with each chamber and associated with a respective lumen of the catheter for establishing fluid communication between each chamber and a respective lumen;
    the housing including a lower housing body and an upper housing body, the lower housing body and the upper housing body each defining internal seating surfaces configured to abut and compress the peripheral flange of each septa therebetween, the upper housing body including at least a pair of latching sections disposed on respective sides thereof to latchingly engage respective corresponding latching sections defined on and by the lower housing body that mechanically secures together the upper and the lower housing bodies in a manner compressing the peripheral flange of each septa and securing the septa in a sealed relationship with the upper and lower housing bodies during needle penetrations into and withdrawal from the septa,
    the latching sections of one of the upper or the lower housing body include latch arms depending therefrom, and the other of the upper or the lower housing body includes recesses along side surfaces thereof within which an entirety of a respective latch arm is disposed upon assembly of the venous access port, thereby providing a smooth continuous exterior surface to the venous access port.

2. The port of claim 1, wherein the latch arms depend from the upper housing body, and the lower housing body includes the recesses along side surfaces thereof within which an entirety of a respective latch arm is disposed upon assembly.

3. The port of claim 2, wherein each latch arm of the upper housing body includes a latch section angularly extending from a free end of the respective latch arm, the latching section establishing a latching connection with a corresponding catch located within a respective and corresponding recess of the lower housing body.

4. The port of claim 1, wherein the two septa are disposed adjacent each other, each including a separate and respective peripheral overlapping flange therebetween, one flange vertically over and covering the other flange.

5. The port of claim 4, wherein the two septa are disposed side-by-side, and wherein the upper housing body includes a plurality of posts depending from a medial rib thereof, and aligned with apertures through the separate overlapping flanges, and the lower housing body includes a plurality of holes aligned therewith, and depending from a medial rib thereof, to receive respective ones of the posts upon assembly, whereby the posts assist in anchoring the septa in position during and after assembly.

6. The port of claim 1, wherein each latch arm includes a latch section angularly extending from a free end of the respective latch arm, the latch section establishing a latching connection with a corresponding catch located within a respective and corresponding recess.

7. A method of assembling an implantable port assembly, comprising the steps of:
provide upper and lower housings and at least one needle-penetrable self-sealing septum, the at least one septum having a peripheral flange and a raised and rounded central portion relative thereto, where at least one of the upper and lower housings includes a plurality of latching sections, and the other thereof includes a like plurality of corresponding latching sections, and where the lower housing body and the upper housing body each define an internal septum seat configured to abut and compress the peripheral flange of the at least one septum therebetween;
positioning the at least one septum into a respective septum seat;
juxtapositioning the upper and lower housings to each other in a manner compressing therebetween the peripheral flange of the at least one septum; and
latching the latching sections with the corresponding latching sections of the other of the upper and the lower housings, wherein the latching sections of one of the upper and the lower housings are latch arms, and the other of the upper and the lower housing includes recesses along side surfaces thereof within which an entirety of a respective latch arm is disposed upon assembly of the venous access port, thereby providing a smooth continuous exterior surface to the implantable port assembly, and wherein the upper and the lower housings are mechanically fastened together during bonding or ultrasonic welding thereof-while the peripheral flange is under compression and secured in a sealed relationship between the septum seats of the upper and the lower housings.

8. The method of claim 7, wherein the latching sections are latch arms depending from the upper housing body, and the lower housing body includes the recesses.

9. The method of claim 8, wherein each latch arm of the upper housing body includes a latch section angularly extending from a free end of the respective latching arm, the latch section establishing a latching connection with a corresponding catch located within a respective and corresponding recess of the lower housing body upon the latching of the latching sections.

10. The method of claim 7, wherein each latch arm includes a latch section angularly extending from a free end of the respective latching arm, the latch section establishing a latching connection with a corresponding catch located within a respective and corresponding recess upon the latching of the latching sections.

11. A venous access port having a housing, two self-sealing septa for infusion by needle, the two self-sealing septa each having a peripheral flange and a raised and rounded central portion relative thereto, the raised and rounded central portion defining a subcutaneous, self-sealing access site for multiple needle sticks, and two reservoirs, wherein the two septa are disposed side-by-side and have adjacent side portions, wherein the adjacent side portions each include a separate and respective overlapping flange therealong, one flange vertically above and covering the other flange, wherein the overlapping flanges assist in securing the two septa in position during and after assembly of the venous access port.

12. The venous access port of claim 11, wherein the housing includes a lower housing body and an upper housing body, wherein one of the upper or lower housing body includes at least one post depending from a medial rib thereof and aligned with a respective aperture through the overlapping flanges, wherein the other of the upper or the lower housing body includes at least one hole aligned therewith, and depending from a medial rib thereof, to receive the at least one respective post upon assembly of the venous access port, wherein the at least one post assists in anchoring the two septa in position during bonding or welding of the venous access port and later during needle penetration and withdrawal.

13. The venous access port of claim 11, wherein the housing includes a lower housing body and an upper housing body, the lower housing body and the upper housing body each defining internal seating surfaces configured to abut and compress the peripheral flange of each septa therebetween, and wherein one of the upper or the lower housing body includes at least a pair of latching arms, each latching arm having a latch section angularly extending from a free end of the respective latch arm, the latch section establishing a latching connection with a corresponding catch defined on and by the other of the upper or the lower housing body that mechanically secures together the upper and the lower housing bodies in a manner compressing the peripheral flange of each of the two septa and securing the septa in a sealed relationship with the upper and the lower housing bodies during needle penetrations into and withdrawal from the septa.

14. The venous access port of claim 13, wherein the latch arms depend from the upper housing body, and the lower housing body includes recesses along side surfaces thereof within which the catch is located, and within which an entirety of a respective latch arm is disposed upon assembly of the venous access port, thereby providing a smooth continuous exterior surface to the venous access port.

15. The venous access port of claim 11, wherein the housing includes a lower housing body and an upper housing body, the lower housing body and the upper housing body each defining internal seating surfaces configured to abut and compress the peripheral flange of each septa therebetween, and wherein at least one of the upper or the lower housing body includes a groove configured to receive a peripheral ridge provided on the upper and lower surfaces of the peripheral flange serving to secure the septa in position.

16. A method of assembling a venous access port having upper and lower housings, two self-sealing septa for infusion by needle, and two reservoirs, the method comprising the steps of:
providing the upper and lowering housings and the two self-sealing septa, the two self-sealing septa each having a peripheral flange and a raised and rounded central portion relative thereto, where at least one of the upper and the lower housings includes a plurality of latching sections, and the other thereof includes a like plurality of corresponding latching sections, and where the lower housing body and the upper housing body each define an internal septum seat configured to abut and compress the peripheral flange of the two septa therebetween;
positioning each septum into a respective septum seat of the upper or the lower housing, wherein the two septa are positioned side-by-side, with adjacent side portions of the two septa each having separate and respective overlapping flanges, one flange vertically above and covering the other flange;
juxtapositioning the upper and the lower housings to each other in a manner compressing therebetween the peripheral flange of each septum; and
latching the latching sections of one of the upper and the lower housings with corresponding latching sections of the other of the upper and the lower housings;
wherein the upper and the lower housings are mechanically fastened together, by the latching, during later bonding or ultrasonic welding together of the upper and the lower housings while the peripheral flange of each septum is under compression and secured between the respective internal septum seats.

17. The method claim 16, wherein the latching sections are latch arms depending from the upper housing body, and the lower housing body includes recesses along side surfaces thereof within which an entirety of a respective latch arm is disposed upon assembly of the venous access port, thereby providing a smooth continuous exterior surface to the venous access port.

18. The method of claim 17, wherein each latch arm of the upper housing body includes a latch section angularly extending from a free end of the respective latch arm, the latch section establishing a latching connection with a corresponding catch located within a respective and corresponding recess of the lower housing body upon the latching of the latching sections.

19. The method of claim 16, wherein juxtapositioning the upper and the lower housings to each other includes inserting at least one post, the at least one post extending from a medial rib of one of the upper or the lower housings, through a respective aperture in the overlapping flanges, and into a respective hole in a medial rib in the other of the upper or the lower housings, the respective hole aligned therewith to receive the at least one respective post, wherein the at least one post serves to secure the housings to each other during bonding or ultrasonic welding of the venous access port.

20. The method of claim 16, wherein juxtapositioning the upper and the lower housings to each other includes inserting at least one post extending from a medial rib of the upper housing through a respective aperture in the overlapping flanges and into a respective hole in a medial rib of the lower housing, the respective hole aligned therewith to receive the at least one respective post, wherein the at least one post serves to secure the housings to each other during bonding or ultrasonic welding of the venous access port.

* * * * *